United States Patent [19]
Gribbin

[11] Patent Number: 5,225,200
[45] Date of Patent: Jul. 6, 1993

[54] NON-MECHANICAL METHOD FOR TREATING MUSCLE CONTRACTURES

[76] Inventor: Dorothea M. Gribbin, 435 E. 70th St., Apt. 23D, New York, N.Y. 10021

[21] Appl. No.: 753,861

[22] Filed: Sep. 3, 1991

[51] Int. Cl.$^5$ .................. A61L 15/16; A61K 31/48; A61K 7/021
[52] U.S. Cl. .................. 424/447; 424/446; 424/78.06; 514/63
[58] Field of Search ............ 514/63; 424/78.05, 78.06, 424/446, 447

[56] References Cited

U.S. PATENT DOCUMENTS

| | | | |
|---|---|---|---|
| 2,727,846 | 12/1955 | Talbot | 514/63 |
| 3,402,243 | 9/1968 | Gerow | 514/63 |
| 3,880,996 | 4/1975 | Fisher | 514/63 |
| 4,983,388 | 1/1991 | Kuwata et al. | 514/63 |

Primary Examiner—Frederick E. Waddell
Assistant Examiner—Raymond J. Henley, III
Attorney, Agent, or Firm—Sherman and Shalloway

[57] ABSTRACT

A method for the treatment of muscle contractures which relies upon the application of polydimethyl siloxane to the skin over the muscle contracture. This pharmacological treatment does not rely upon mechanical stretch of muscle and connective tissue and therefore, is particularly useful for the treatment of muscle contractures in patients where traditional mechanical methods of treatment are contraindicated due to underlying physical disorders.

9 Claims, No Drawings

NON-MECHANICAL METHOD FOR TREATING MUSCLE CONTRACTURES

BACKGROUND OF THE INVENTION

This invention relates to a method for treating patients suffering from muscle contractures. More particularly, this invention relates to the use of polydimethyl siloxane (silicone) polymer-treated dressings in the treatment of muscle contractures. The inventive method is particularly useful in the treatment of patients who present contraindications to traditional methods for treating muscle contractures.

DESCRIPTION OF THE PRIOR ART

Muscle contracture is a common complication of immobilization. Basically, immobilized limbs that remain in the same position for a long time are prone to stagnation. Decreased range of motion of the peripheral joints ensues due to disuse of the muscle and the development of contractures. Contracture of the length of the muscle is a consequence of thickening and "shrinkage" of the muscle connective tissue, the perimysium and epimysium.

Traditional methods for treating simple muscle contractures include manual stretching, positioning, dynamic splinting and serial casting. These methods, which rely upon mechanical stretching of muscle and surrounding connective tissue are often very painful and require a treatment time ranging from weeks to months. These methods also require frequent monitoring by medical personnel to prevent skin ulcers, spontaneous bleeding or neurological compromises due to compression. Moreover, the pathophysiology of the condition, including loss of sarcomeres and reduction in muscle fiber length encountered in therapeutic mechanical stretching of the effected muscle.

Patients suffering from a hematological disorder, such as, for example, hemophilia or sickle cell anemia, and patients with pre-existing skin ulcerations, sensory deficits, osteoporotic or metastatic bone disorders are contraindicated for traditional treatments for muscle contracture, since the use of mechanical stretch may exacerbate the underlying condition. These patients are left without any option for treatment of muscle contractures and consequently, their mobility and performance of simple activities is severely limited. The need for improved therapies for muscle contractures is thus quite evident.

Polydimethyl siloxane (silicone) has been widely used in the treatment and prevention of several disorders including skin contractures associated with burns and wounds. Silicone is an inert hydrophobic, non-volatile cross-linked dimethyl and vinyl end blocked polydimethyl-siloxane polymer having a specific gravity of about 0.955. The beneficial action of topical silicone for burn treatment was first described by Adamczak, et al., Ploshi Tygodnik Lekarski (1961) 16, 659-664. It has since been topically applied as a gel to burns, burn scars and scar-induced joint contractures (Perkins, et al., Burns (1983) 9, 201-204; Perkins, et al., Burns (1983) 13, 406-410). It has also been used in the prevention of poison ivy (Eplein, WL., Arch. Dermatol. (1989) 125, 449-501).

The mode of action of silicone in the above-mentioned applications is unknown. Investigation of the effects of silicone on hypertrophic scars indicates that scar reduction is not due to pressure, occlusion, tension or alteration of temperature or oxygen availability. Silicone is, therefore, regarded as a pharmacological agent rather than a treatment dependent on its physical properties.

It is an object of the invention to provide a pharmacological method of treating muscle contractures in patients, which does not rely upon mechanical stretching of muscle and connective tissue.

According to the present invention, there is provided an improved method of treating muscle contractures which provides improved range of motion in a relatively short period of time.

It is another object of the invention to provide a method of treating muscle contractures in patients whose underlying physical disorder is contraindicative of traditional contracture treatment methods.

It is a further object of the invention to provide a method of treating muscle contractures that is inexpensive, simple and painless.

SUMMARY OF THE INVENTION

The present inventors have designed a method for the treatment of muscle contractures. This invention relates to a method for treating muscle contractures in patients, which comprises applying methylsiloxane polymer directly to the skin in the area over the contracture, applying a bandage over the silicone-treated skin, allowing the bandage to remain in place continuously for an effective amount of time to allow the methylsiloxane polymer to permeate the skin. Such treatment results in improvement of the muscle contracture evidenced by an increased range of motion of the treated joint. The bandage may be removed for cleansing, after which methyl siloxane and bandage are reapplied.

In another embodiment of the invention, a silicone-treated bandage is applied to the area of skin directly over the muscle contracture. The silicone-treated bandage may be further treated with an antifungal agent, an antibacterial agent, antiseptic or other substance employed in the treatment of wounds.

In another embodiment of the invention, a silicone-treated form-fitting supportive bandage for a human joint is applied to the muscle contracture.

DETAILED DESCRIPTION OF THE INVENTION

The present invention represents a departure from the traditional approach to the treatment of muscle contractures. In particular, the improved method of treatment of the invention provides a much needed therapy for patients whose underlying disorders contraindicate the use of established treatments, which include manual stretching, positioning, dynamic splinting and serial casting. Such patients include those with pre-existing skin ulcerations, sensory deficits, hematological disorders and osteoporotic or metastatic bony disorders. Those patients were previously left without any option for treatment of muscular contractures which severely limited their mobility.

In general, the invention relates to a novel pharmaceutical treatment of muscle contractures which provides superior results compared to traditional treatments. The invention provides a novel, simple, inexpensive and effective treatment for increasing the range of motion of permanently contracted muscles. Moreover, the materials used to practice the invention treatment are commercially available and easily obtained.

Conceptually, the improved results in muscle range of motion produced by the improved and novel method of treatment of the invention, include a painless and shortened period of treatment, widespread applicability to various types of intrinsic muscle contractures and the elimination of need for aggressive treatment and frequent patient monitoring.

There are various types of muscle contractures. Contractures due to anatomical changes are generally classified as myogenic, soft tissue shortening or arthrogenic. In all cases, limitation of active and passive range of motion leads to further reduction of mobility. With time, intact structures are secondarily affected by reduced mobility and there is a proliferation of collagen in the endomysium and perimysium. Changes in all tissues surrounding the joint may ultimately contribute to long-standing contractures.

Contractures may be caused by intrinsic or extrinsic processes. Extrinsic factors involve neurological or anatomical abnormalities, for example. Intrinsic processes include, for example, inflammation, infection, ischemia, hemorrhage, degenerative or traumatic processes. The method of this invention is specifically applicable to the treatment of myogenic contractures of intrinsic etiology.

It has now been found that the application of a cross-linked silicone coating directly to the skin over a muscle contracture results in rapid improvement in the range of motion of the muscle.

Silicones are a group of synthetic polymers containing the recurring group, —Si $R_2O$— wherein R is a radical such as an alkyl, aryl, phenyl or vinyl group. Simple silicones are oils of very low melting point, while complex silicones are highly cross-linked and typically rigid solids. Intermediate physical properties are exhibited by silicone elastomers such as silicone gels or rubbers.

According to the methods of the present invention, silicone gels are used in treatment of contractures. The cross-linked silicone gels used in the invention may release silicone oils. The cross-linked silicone may be tacky gel, which makes it easy to apply and will usually remain in place while a bandage is applied or may be non-tacky.

The cross-linked silicones may be formed from linear silicones having reactive groups thereon. The reactive groups that cause the cross-linking reaction may be silanol groups. Preferably, the silicone gels used in the present invention are formed by reaction between a vinyl-substituted silicone and a hydride-containing silicone in the presence of a suitable catalyst.

Various types of silicone previously shown to be useful in the treatment of the human body, i.e. for the treatment of burns, are disclosed in U.S. Pat. Nos. 4,991,574, 4,034,751 and 4,838,253. These references are incorporated herein by reference thereto.

According to the method of the present invention, the silicone elastomer may be directly applied to the skin over the muscle contracture. The silicone-treated area is then covered by a bandage, which may, for example, comprise a woven or non-woven or knitted mesh, such as cotton gauze. The bandage may comprise an absorbant pad to absorb exudate or a cushioning pad. Such pads may be of conventional construction, and may be formed from such materials as, for example, cellulose fibers super-adsorbents and hydrophilic foams. In a preferred embodiment, a form-fitting bandage of the appropriate size and shape is applied to the silicone-treated area surrounding the muscle contracture. Such form-fitting bandages are commercially available and may comprise an elasticized fabric suitable for wrapping about a human limb or joint, such as the knees or elbows.

The bandage may be secured to the patient in any convenient manner, such as by adhesive tape or other fastening elements. The bandage is left in place, allowing the silicone to permeate the skin and reach the subdermal layers of tissue, such as collagen in the perimysium and endomysium. The bandage may be removed for cleansing, after which silicone is re-applied and the area re-bandaged.

In an alternative method, a silicone treated bandage may be directly applied to the area over the muscle contracture. Such bandages are commercially available, for example, from Johnson & Johnson, Dow Corning Wright and Spenco Medical Corporation and are typically used for severe burn treatment.

The bandage may further comprise an antifungal agent, antibacterial agent, antiseptic, or any other substance employed in the treatment of wounds or any combination thereof. Such bandages are useful in the treatment of muscle contractures in patients with open wounds in the dermal layers in the area around the muscle contracture. Typically, such bandages will be sterilized, e.g. by $\gamma$ irradition. In this embodiment, the bandage is directly applied to the wound area thereby allowing the wound treating substance to penetrate the wound, as well as allowing the silicone to penetrate through the skin and wound to the subdermal tissues. Typically, the bandage will comprise an absorbant pad. The bandage may be replaced as often as necessary.

The bandage is left in place, except during cleansing, for a therapeutically effective amount of time. The skilled practitioner in the art will be able to determine the amount of treatment time required. Typically, a treatment period of about 3 to about 14 days is sufficient to provide improvement of range of muscle motion of about 5° to 50°, depending on the extent and location of the contracture, as well as, such factors as underlying physical conditions of the patient.

In the present invention there is no need for direct contact between the silicone and underlying muscle and tendons. In this respect, the present use of silicone differs from all previous treatments utilizing silicone where the gel is applied directly to the skin lesion or skin contracture. Instead, in the present invention, silicone is applied topically and permeates the skin to reach connective tissue defects of deeper tissues.

The mechanism of action of silicone is unknown. It is notable, however, that muscle contractures treated with topical applications of silicone to intact skin dramatically and rapidly improved. This ability of silicone to reach deeper tissues strongly suggests a pharmacological rather than physical mechanism of action.

While the exact pharmacological action of silicone is unknown, it appears to act on collagen in the perimysium and endomysium and may either decrease the collagen content and/or alter collagen cross-linkage to increase elasticity.

Sheets of silicone gel applied to filter paper have been shown to produce a stain after several hours. Quinn, et al. Burns (1985) 12: 102–108. It is possible that some of the oily fluid released from the silicone penetrates the skin. Although the chemical composition of the released fluid is unknown, it may be expected to contain lower molecular weight silicone polymers, polymerization monomers, or traces of catalysts and modulators used during polydimethyl siloxane synthesis. It is possible that some of these substances directly affect muscle collagen.

It has also been established that contact with polydimethyl siloxane polymer activates macrophages and related cells and stimulates them to produce a variety of cytokines and other bioeffector molecules. Ziats, et al. Biomaterials (1988) 9: 5–13. Macrophages contacting the silicone gel or fluid released by the silicone may be activated and may contribute to the therapeutic effect of the invention method. Macrophages or cells responding to the cascade of macrophage products may be responsible for collagen remodelling and relief of muscle contractures. Improvement in skin elasticity may also contribute to the observed therapeutic effect of the invention.

Excellent therapeutic results have been reported previously with the use of topical silicone in skin disorders and in scar management. Many burn patients have avoided reconstructive surgery of contracted joints through use of polydimethyl siloxane polymer treatment. Silicone applied to healed, partial-thickness burns decreases the incidence of hypertrophic scars and softens already formed scars. Other than a heat rash reaction in hot climates, there have been no adverse reactions or side effects of topical silicone in 25 years of use.

The method of the invention is further illustrated in the following clinical study.

The method of the invention was used randomly in the treatment of muscle contractures in 7/14 patients having contraindications to traditional therapy. Their muscle contractures were chronic and had been fixed or unchanging for 60 to 5,900 days prior to therapy. A control group consisting of 7 patients received no treatment.

Two members of the control group had developed knee flexion contracture as a result of long standing immobility due to peripheral vascular disease complications. Two other control group patients suffered from longstanding non-healing ulcers of the lower extremities leading to immobilization and contractures. Three patients in the control group were bedridden and immobilized for prolonged periods due to multiple medical problems and altered mental status. Each of these three patients had various muscle contractures.

The other 7 patients in the study received treatment for muscle contractures by the method of the present invention. Basically, polydimethyl siloxane treated bandages were applied topically over the area of the contracted muscles, attached with porous tape and left in place continuously, except during cleansing, after which, the original bandages were immediately reapplied.

The patients were evaluated after 24 hours and then after every 48 hours. The degree of active joint range of motion was measured at each evaluation by the same physician trained in using full circle 360° goniometry, which is accurate within 4°.

In the treated group there was a dramatic improvement in range of motion with a mean improvement of 26°±17° after 3 to 14 of days of treatment (mean of 7.5±3 days). The results are summarized in Table 1.

TABLE 1

| Pt. # | Age | Sex | Race | 1° Diagnosis | Contracture Location | °Flex Pre-treatment | °Flex Post-treatment | Duration of Treatment |
|---|---|---|---|---|---|---|---|---|
| 1 | 30 | M | Caucasian | hemophilia; active bleeding | knee | 120° | 155° | 10 days |
|  |  |  |  |  | rt. knee | 135° | 160° | 10 days |
|  |  |  |  |  | lt. knee | 170° | full extension | 10 days |
| 2 | 63 | F | Black | peripheral vascular disease | knee | 100° | 150° | 5 days |
| 3 | 30 | M | Black | sickle cell anemia in actue sickle cell crisis | rt. knee | 0° | 10° | 7 days |
|  |  |  |  |  | lt. knee | 0° | 5° | 7 days |
| 4 | 30 | F | Black | sickle cell anemia; non-healing ulcer | ankle | 45° | 90° | 3 days |
| 5 | 49 | M | Black | peripheral vascular disease; ulcer | knee | 90° | 135° | 14 days |
| 6 | 49 | F | Black | tuberculosis; liver failure; sepsis with intravascular coagulation | *rt. plantar-flexion contracture | 135° | 122° | 10 days |
|  |  |  |  |  |  | 125° | 115° | 10 days |
| 7 | 89 | M | Caucasian | artial fibrillation requiring anti-coagulation | *rt. plantar-flexion contracture | 125° | 90° | 5 days |

*Plantar-flexion contracture improvement is measured by a decrease in °Flex.

I claim:

1. A method of treating muscle contractures in patients which comprises the steps of
   (1) topically applying a polydimethyl siloxane polymer directly to the skin over the contracture;
   (2) covering the skin over the contracture with a bandage; and
   (3) allowing the bandage to remain in place continuously for an effective amount of time to allow the polydimethyl siloxane to permeate the skin, whereby the muscle contracture is improved with an increased range of motion.

2. The method of treating a muscle contracture according to claim 1 which further comprises removing the bandage, cleansing the area under the bandage, after which polydimethyl siloxane polymer and bandage are reapplied.

3. The method of treating muscle contractures according to claim 1, wherein the effective amount of time for treatment is in the range of about 3 to about 14 days.

4. The method of claim 1 wherein the polydimethyl siloxane polymer is in the form of a gel.

5. The method of claim 1 wherein the bandage comprises a cushioning pad.

6. The method of claim 1 wherein the bandage is a form-fitting bandage of the appropriate size and shape of the area being treated.

7. A method of treating muscle contractures in patients which comprises the steps of
   (1) applying a polydimethyl siloxane polymer-treated bandage directly to the skin over the contracture, and
   (2) allowing the bandage to remain in place continuously except during any cleansing of the area under the bandage, after which the original sheet is immediately reapplied, for an effective amount of time whereby the polydimethyl siloxane permeates the skin and contributes to the improvement of the muscle contracture.

8. A method of treating a muscle contracture in a patient having an open wound in the area of the muscle contracture which comprises the steps of
   1) topically applying a bandage comprising an absorbant pad treated with polydimethyl siloxane polymer and at least one of an antiseptic, antibacterial agent, antifungal agent, or any combination thereof,
   2) allowing the bandage to remain in place for an amount of time effective to allow the polydimethyl siloxane to permeate the skin and to allow the antiseptic, antifungal agent, antibacterial agent, or mixture thereof, to penetrate the wound, whereby the muscle contracture is improved with an increased range of motion.

9. The method of claim 8 wherein the bandage is sterilized prior to step 1.

* * * * *